United States Patent [19]

Vale et al.

[11] Patent Number: 4,864,019

[45] Date of Patent: Sep. 5, 1989

[54] ANTIBODIES TO INHIBIN AND CONJUGATES PRODUCED THEREFROM

[75] Inventors: Wylie W. Vale; Jean E. F. Rivier, both of La Jolla; Joachim Spiess, Encinitas, all of Calif.

[73] Assignee: The Salk Institute for Biological Studies, San Diego, Calif.

[21] Appl. No.: 91,695

[22] Filed: Aug. 31, 1987

Related U.S. Application Data

[63] Continuation-in-part of Ser. No. 796,300, Nov. 8, 1985, abandoned, which is a continuation-in-part of Ser. No. 785,345, Oct. 7, 1985, abandoned.

[51] Int. Cl.$^4$ .......................... A61K 35/14; C07G 7/00
[52] U.S. Cl. .................... 530/387; 530/388; 530/389; 525/54.1
[58] Field of Search ............... 530/350, 388, 389, 387; 525/54.1

[56] References Cited

U.S. PATENT DOCUMENTS 4,474,757 10/1984 Arnon et al. ........................... 424/88
4,493,795 1/1985 Nestor, Jr. et al. .................. 530/328
4,740,587 4/1988 Ling et al. ........................... 530/313

FOREIGN PATENT DOCUMENTS

WO86/00078 1/1986 World Int. Prop. O. .

OTHER PUBLICATIONS

D. M. Robertson et al., "Isolation of Inhibin from Bovine Follicular Fluid", B.B.R.C., 126, No. 1, 220–226 (1985).
Jean Rivier et al., "Purification and Partial Characterization of Inhibin from Porcine Follicular Fluid", B.B.R.C., 133, No. 1, 120–127 (1985).

Primary Examiner—Morton Foelak
Assistant Examiner—Nathan M. Nutter
Attorney, Agent, or Firm—Fitch, Even, Tabin & Flannery

[57] ABSTRACT

A 32,000-Dalton protein with inhibin activity is isolated from porcine follicular fluid which is composed of two chains having molecular weights of about 18,000 and about 14,000 Daltons, which are bound together by disulfide bonding. Microsequencing revealed the $NH_2$-terminal portion of the 18 kD chain to be Ser-Thr-Ala-Pro-Leu-Pro-Trp-Pro-Trp-Ser-Pro-Ala-Ala-Leu-Arg-Leu-Leu-Gln-Arg- Pro-Pro-Glu-Glu-Pro-Ala-Val and of the 14 kD chain to be Gly-Leu-Glu-Cys with the next 21 residues believed to be Asp-Gly-Ser-His-Asn-Leu-Asp-Ser-Arg-Gln-Gln-Phe-Phe-Ile-Asp-Phe-Arg-Leu-Ile-G y-Trp. This 32 kD protein specifically inhibits basal secretion of FSH, but not of LH. Antibodies raised against a synthetic replicate of the N-terminal six residues of the 18 kD chain are effective to reduce the activity of highly purified 32 kD inhibin and may be administered to mammalian animals for the purpose of neutralizing endogenous inhibin and thereby increasing gonadotropin secretion. The antibodies are also useful in immunoassays to determine inhibin levels in mammalian fluids. To generate the antibodies, short chain peptides are synthesized which mimic portions of natural mammalian inhibin protein chains, the synthetic peptides are conjugated to large carrier molecules and the conjugates are used as inoculum to induce a mammalian immune system to produce inhibin-reactive antibodies.

15 Claims, 1 Drawing Sheet

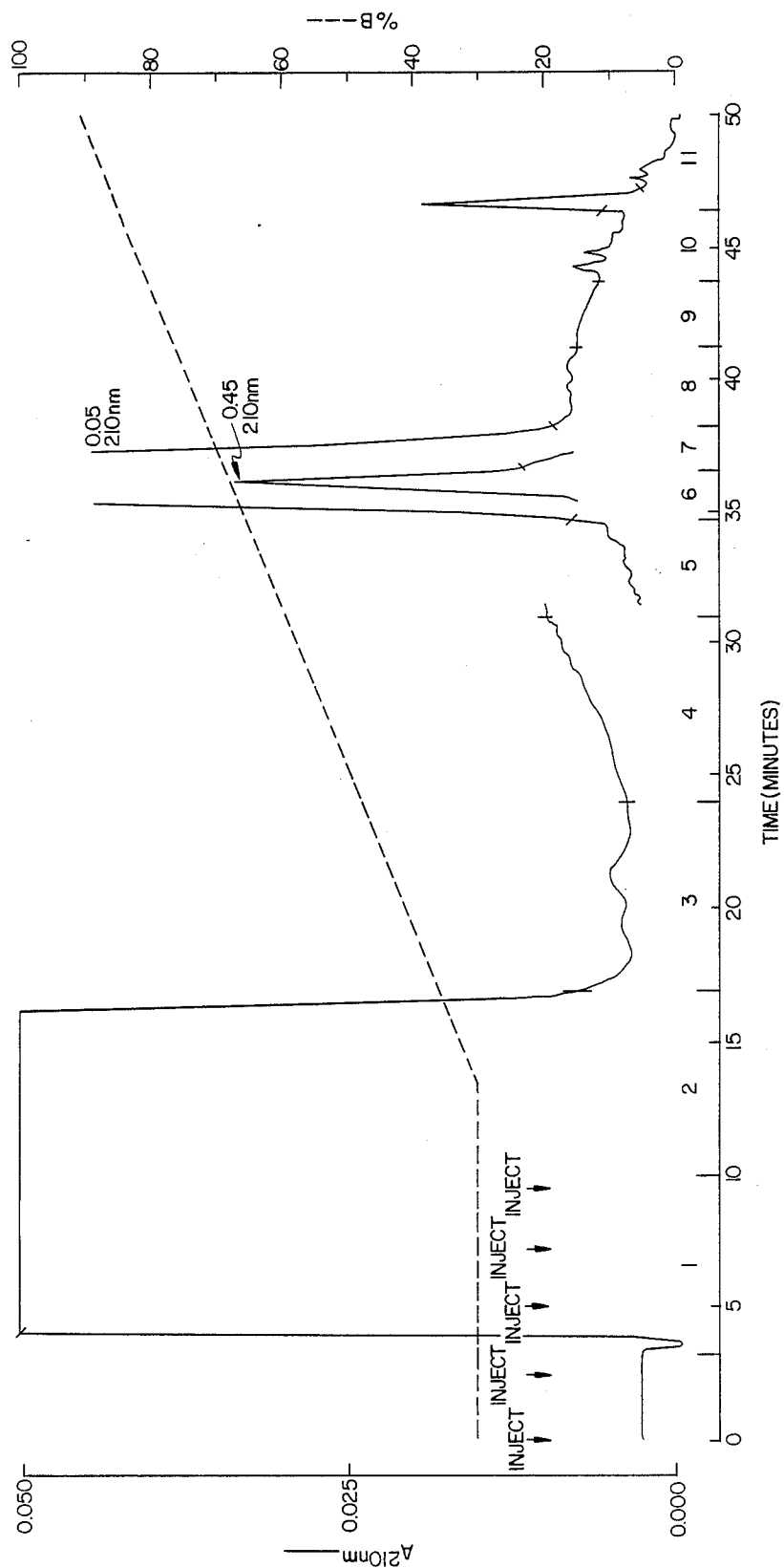

ANTIBODIES TO INHIBIN AND CONJUGATES PRODUCED THEREFROM

This invention was made with Government support under Grants HD-13527 and AM-26741 awarded by the National Institutes of Health. The Government has certain rights in this invention.

This application is a continuation-in-part of U.S. patent application Ser. No. 796,300, filed Nov. 8, 1985 and now abandoned, which is a continuation-in-part of U.S. patent application Ser. No. 785,345, filed Oct. 7, 1985, now abandoned.

The present invention relates to antibodies which are effective to reduce the inhibin activity of native inhibin.

BACKGROUND OF THE INVENTION

The existence of inhibin as a water-soluble substance of gonadal origin which acts specifically at the pituitary level to suppress the secretion of follicle-stimulating hormone (FSH) was postulated by McCullagh more than 50 years ago, Science, 76, 19–20 (1932). There has been great interest in it, and many laboratories have attempted to isolate and characterize this substance. Many reports have appeared in the literature claiming the purification of inhibin-like material; however subsequent studies have shown that these substances were either not homogeneous or did not have the high specific activity of true inhibin. Inhibin may be used to regulate fertility, gonadotropin secretion or sex hormone production in mammalians, both females and particularly males.

SUMMARY OF THE INVENTION

In accordance with the present invention, antibodies are produced which are reactive with mammalian inhibins and block the hormonal activity of the inhibins. In particular, antibodies are developed which react with the N-terminus of the chains of mammalian inhibins, inactivating the hormonal activity of the same. Mammalian inhibins blocked by prior reaction with antibodies lose their ability to inhibit pituitary secretion of FSH. If administered to mammalian animals, inhibin-reactive antibodies react with and neutralize the activity of the animals' endogenous inhibins. Accordingly, the biological effect of administering inhibin-reactive antibodies is opposite to the effect of administering mammalian inhibin, namely, that secretion of FSH is increased due to depressed levels of endogenous inhibin. Inhibin-reactive antibodies are useful in regulating fertility, gonadotropin secretion or sex hormone production in mammalians, both females and particularly males. Synthetic inhibin antigens may also be used in immunoassays to compete with endogenous inhibin of mammalian fluids, such as blood serum, for binding sites of inhibin-reactive antibodies. Abnormal levels of inhibin in mammalian fluids, as assayed by immuno techniques, may indicate the cause of fertility problems in mammalian animals.

A protein having a molecular weight of about 32,000 Daltons (32 kD) and having inhibin activity has been successfully isolated from porcine follicular flui(pFF). The protein has been partially characterized using microsequencing methods.

The protein was isolated to substantial homogeneity from material obtained from pFF and is hereinafter referred to as inhibin. The protein has a molecular weight of about 32 kD and is composed of two polypeptide chains having molecular weights of 18,000 and 14,000 Daltons, respectively, the chains being linked together in the biologically active protein by disulfide bonding. The amino-terminal residue sequence of the larger 18 kD chain (or alpha chain) of the protein is Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val. The amino-terminal of the 14 kD chain (or beta chain) begins Gly-Leu-Glu-Cys. The 32 kD protein exhibits inhibin activity in that it specifically inhibits the basal secretion of FSH but does not inhibit secretion of luteinizing hormone (1H). Antibodies raised against a synthetic replicate of the N-terminal six residues of the of the 18 kD chain were surprisingly found to be effective to reduce the biological activity of inhibin.

Purification of porcine inhibin to substantial homogeneity, i.e., about 90% by weight of total protein in the fraction, was achieved through a combination of protein separation procedures including gel filtration and reverse-phase, high-performance liquid chromatography (RP-HPLC).

BRIEF DESCRIPTION OF DRAWING

The FIG. is a chromatogram of RP-HPLC purification of inhibin protein active fractions from Step 8 of Table 1 which were pooled and applied in 5 injections directly onto a 0.46×25 cm Vydac $C_4$ column with a 5 $\mu$m particle size and a 300A pore size, and eluted with the indicated gradient of buffers from 30% Buffer B to 65% Buffer B in 20 minutes as shown by dotted lines, at a flow rate of 0.7 ml/min. with a back pressure of 1200 psi.

DETAILED DESCRIPTION OF THE PREFERRED EMBODIMENT

In accordance with the present invention, antibodies have been developed which react with inhibin and thereby block the FSH secretion-stimulatory action of the inhibin. Inhibin-reactive antibodies are administered to a mammalian animal to reduce the effective amount of endogenous inhibin. This results in an increase in secretion of FSH by the animal's pituitary and thus affects the fertility of the mammalian animal. Administration of inhibin-reactive antibodies is useful in enhancing male fertility, may be useful to both control ovarian cycles and likely increases multiple births in certain species.

In accordance with a preferred aspect of the present invention, antibodies are produced which are reactive with a specific portion or site of an inhibin polypeptide chain in a manner which blocks the hormonal activity of the inhibin protein. It is found, for example, that an antibody that reacts with the N-terminus of the alpha chain of porcine inhibin neutralizes the hormonal effects of the inhibin molecule.

Using a multi-step procedure, the 32 kD peptide was isolated to substantial homogeneity from porcine follicular fluid (pFF). The protein is composed of two chains of 18 kD and 14 kD, and the chains of the intact molecule are held together by disulfide bonding, the linkage between the chains being necessary for biological activity. An amino acid analysis of the total protein has been performed, and a partial amino acid residue sequence of each chain has been determined, beginning at the amino-terminus. The chains are rich in Cys residues, and it is believed that internal disulfide bonding is also present. The amino-terminal sequence of the 18 kD chain is Ser-Thr-Ala-Pro-Leu-Pro-Trp-Pro-Trp-Ser- Pro-Ala-Ala-Leu-Arg-Leu-Leu-Gln-Arg-Pro-Pro-Glu-Glu-Pro-Ala-Val. The 18 kD chain is estimated to be about 135 to about 150 residues in length and is linked by one or more disulfide bridges to the 14 kD chain. The 14 kD chain has between about 115 and 130 residues and clearly begins at the N-terminus with the following sequence: Gly-Leu-Glu-Cys. The next seven residues are believed to be: Asp-Gly-Ser-His-Asn-Leu-Asp. The fourteen residues following these seven are believed to be: Ser-Arg-Gln-Gln-Phe-Phe-Ile-Asp-Phe-Arg-Leu-Ile-Gly-Trp. The C-terminus of either chain may be amidated or free acid.

The sharp elution peak of the protein which was obtained in the final chromatographic purification step is evidence that the protein has been purified to at least about 90% by weight of total protein. The 32 kD protein is water-soluble, and one of the forms of the native protein is likely glycosylated. Another appears to be a precursor form in which an N-extended precursor of the 18 kD chain, that is greater than 40,000 Daltons, is linked to the 14 kD chain.

The 32 kD protein exhibits inhibin activity in that it specifically inhibits basal secretion of FSH in a rat anterior pituitary monolayer culture system and exhibits a half-maximal effective dose ($EC_{50}$) of 0.3 ng/ml (10 pM.), based upon the assay described in detail in *Endocrinology*, 113, 1121–31 (1983). The isolated 32 kD protein, as well as partially purified inhibin preparations, blocks the secretion of both 1H and FSH in vitro when cells are stimulated by gonadotropin releasing hormone. In vivo, partially purified inhibin preparations are highly selective to decrease plasma FSH and not LH levels. The effects of inhibin on basal gonadotropin secretion in vitro appears to best reflect the in vivo situation. The 32 kD protein is useful for regulating gonadotropin secretion and thus fertility and or sex hormone production of both male and female mammalians. The possibility that inhibin might have direct gonadal actions on gametogenesis or steroidogenesis is also likely, and some brain actions of inhibin are suggested.

Two similar purification procedures were used to isolate porcine inhibin from crude pFF, both utilized successive purification steps that include Reverse Phase-High Performance Liquid Chromatography (RP-HPLC) with different stationary phases and/or mobile phases and gel filtration or permeation Fast Protein Liquid Chromatography(FPLC).

The starting material for the procedure was either 3000 ml. or 6050 ml. of pFF that was procured from the Contraceptive Development Branch of NICHD. The pFF was processed in 500 ml batches to isolate the inhibin. One purification procedure utilized organic solvent precipitation whereas the other utilized ammonium sulfate precipitation.

In each procedure, a 500 ml bottle of frozen pFF is thawed, and the cell debris is separated in a centrifuge at 700 rpm for 5 minutes. The crude supernatant contains the active inhibin procedure and averaged 65 mg protein per milliliter of pFF.

In the organic solvent precipitation, about 3000 ml of the crude supernatant was brought up to six liters with TEAP, pH 5.0. Next, 4 liters of n-Propanol was slowly added to the solution while stirring; a precipitate was generated and centrifuged at 1700×g for ten minutes. The pellet was then washed three times with 40% propanol/60% TEAP, pH 5.0, buffer, and the supernatants were pooled, all percents being by volume. The supernatant was then diluted with deionized water until it contained about 10% n-propanol, filtered through a 5 μm membrane, loaded onto a Waters preparative HPLC using a Vydac $C_4$ cartridge and eluted as described in Table 1, Step 1. Recovery of bioactivity was approximately 10%.

When the ammonium sulfate precipitation purification procedure was employed, an equal volume of Schwartz/Mann ultrapure 100% saturated ammonium sulfate adjusted to pH 7.8 with ammonium hydroxide was added dropwise, over 2-3 hours at room temperature (RT) to the supernatant. The mixture was centrifuged at 8200 rpm for 30 minutes at RT. Supernatant and precipitate were separated; and the supernatant was ultrafiltered and concentrated using a Millipore Pellicon Cassette setup with 5 square feet of filters of 10,000 MW cut off. The filtering retentate was washed with deionized $H_2O$, 10 mM Hepes and 0.05% dimethylsulfide, pH 7.5. The supernatant was recirculated through the cassette system at a rate of 300 ml/min using a peristalic pump, and back pressure was applied until filtration rate was 20 ml/min. After concentration, the retentate (2.5 liters) was washed three times with 4 times its volume of buffer. The retentate was collected (6,050 ml-eq in 2.24 liters). Overall recovery of biological activity was approximately 13%. Protein concentration (determined by amino acid analysis after acid hydrolysis) was 10 mg/ml-eq.

Preparative HPLC was carried out as described in Rivier et al., *J. Chromatography*, 288, p. 303–328 (1984) under the conditions reported in Table I for Steps 1 and 2 with respect to both purification procedures. A cartridge was used in Step 1 for 2 runs only since interfering substances which could not be eluted from the silica between runs seemed to accumulate at the top of the cartridge. Semi-preparative and analytical HPLC steps 3, 4, 6, 7 and 9 are described in Table I. Steps 5 and 8 (Table I) were gel permeation separations carried out under denaturing conditions using a Pharmacia FPLC, S-12B, 1×30 cm column in 6M Guanidine.HCl, 0.1M $NH_4OAc$, pH 4.75 and 0.5% dimethylsulfide(DMS). The final step of purification led to a desalted preparation, and the chromatogram of this step is illustrated in FIG. 1. The ammonium sulfate purification procedure included an additional step (as Step 2A) which was a gel permeation step using a Pharmacia Bioprocess column 25.2×120 cm, filled with 52 liters of Sepharose CL-6B. Eluant was 6 M quanidine-HCl, 0.1 M ammonium acetate, ph 4.75 with 0.05% dimethyl sulfide. Flow rate was 1100 ml/hour.

Purification by RP-HPLC was carried out at 60° C. for Steps 1 and 2 and thereafter at RT. The inhibin protein fractions from the various columns used for the previous step are pooled for each following step; the size of each sample that is processed being set forth in the first column of Table 1. In Step 1, for example, the filtrate from the membrane treatment was applied directly onto a 5×30 cm Vydac 20-μm particle-size $C_4$ column (The Separations Group, Hesperia, Calif.) and eluted using a gradient of TEAP buffer. In the TEAP system for Step 1, Buffer A consists of 0.1 N. triethylammonium phosphate(TEAP) pH 5, and Buffer B is 60% n-propanol in Buffer A. After all the filtrate had been loaded, the column was washed with the aqueous buffer A until the UV absorption reached baseline. Flow through the column is maintained at 50 ml per minute, and the gradient for the mobile phase was then begun at 10% Buffer B, gradually changing to 60% over 45 minutes. The fractions are separated by an Altex 420 gradient liquid chromatography system equipped with a Spectroflow 773 UV detector (Kratos Analytical Instruments, Ramsey, N.J.) and a Servocoder SR 6253 strip chart recorder and are collected and tested for substantial inhibin activity.

Inhibin protein fractions from the various individual columns were pooled and further purified by three more RP-HPLC steps. Step 2 uses a 5×30 cm Vydac 20-μm-particle-size $C_4$ column, a TEAP buffer of higher pH. Step 3 employs a 1×30 cm Vydac 5-μm-particle-size $C_4$ column and a trifluoroacetic acid (TFA) buffer system. In the TFA system, Buffer A contains 1 ml trifluoracetic acid in 999 ml water and Buffer B is 400 ml of water, 1 ml of TFA and 599 ml of acetonitrile. Step 4 employs a 0.46×25 cm Vydac 5-μm-particle size $C_4$ column, with a different elution pattern.

In the purification procedure which utilized the ammonium sulfate precipitation, the inhibin protein fractions accumulated from all the batches following Step 2 were fractionated by gel filtration to separate proteins generally according to their molecular weights by applying to 1×30 cm Sepharose(FPLC) 12-B columns (Pharmacia Fine Chemicals, Piscataway, N.J.). Each column was eluted with 6M guanidine.HCl, 0.1M ammonium acetate, pH 4.75, and 0.5% DMS at a flow rate of 0.4 ml per minute for about 50 min. The column fractions were monitored by UV absorption and by bioassay.

In both purification procedures, inhibin protein fractions from the various individual columns following Step 4 were pooled and further purified by two gel permeation separations and three more RP-HPLC steps using 5-μm-particle-size $C_4$ columns.

A chromatogram of Step 9 is depicted in FIG. 1 and was generated using an Altex 420 System, two Beckman Model 100A pumps, a Datamark, Servocoder SR 6253 strip chart recorder, a Kratos, Spectroflow 773 variable wavelength, UV/visible detector and a Rheodyne 7125 injector with a 2.0 ml loop. 560 ml-eq of pFF in 5.0 ml was applied in 5 equal injections at the specified times to a 0.46×25 cm Vydac $C_4$ Column of reversed phase material with a 5 μm particle size and a 300A pore size. Buffer A is 0.1% (v/v) TFA in water and Buffer B is 1 ml TFA, 200 ml of water and 799 ml of acetonitrile. Flow rate was 0.7 ml/min with a back pressure of 1200 psi and a detector setting of 210 nm, 0.05 AUFS, which was changed to 0.45 AUFS during elution of the peak. Buffer B was used at 30 volume % for about the initial 13.5 minutes and then at a gradient from 30% to 65% in twenty minutes as shown by dotted lines, and continued to increase thereafter. The purified inhibin protein eluted generally between about 20.5 minutes and about 22.5 minutes after start of the gradient, which is equal to between about 14.3 and about 15.5 ml elutant after start of the gradient.

Finally, the inhibin protein fractions accumulated from all batches were pooled, resulting in a total of approximately 7 μg of inhibin protein from about 3000 ml of pFF using the organic solvent precipitation and in a total of about 19 μg of inhibin protein from about 6000 ml of pFF using the ammonium sulfate precipitation.

Amino acid analyses of the substantially homogeneous inhibin protein was performed after acid hydrolysis in 4M methane sulfonic acid and 0.2% tryptamine at 110° C. for 24 hours. Because of the presence in some hydrolysates of contaminants, possibly amino sugars, which interfered with the quantitation of norleucine, 4-fluoro-phenylalanine was used as internal standard instead of norleucine. The amino acid analyzer was a Beckman Model 121M with ninhydrin post-column derivation. The results are shown in Table 1 below.

TABLE 1

| AMINO ACID COMPOSITION OF PURIFIED INHIBIN PROTEIN FROM PORCINE FOLLICULAR FLUID | |
|---|---|
| Amino Acid | Inhibin Protein |
| Asx | 23 ± 3 |
| Thr | 11 ± 2 |
| Ser | 23 ± 6 |
| Glx | 23 ± 3 |
| Gly | 27 ± 3 |
| Ala | 20 ± 2 |
| Val | 10 ± 3 |
| Met | 2 ± 2 |
| Ile | 10 ± 3 |
| Leu | 24 ± 2 |
| Tyr | 9 ± 2 |
| Phe | 10 ± 2 |
| His | 13 ± 2 |
| Trp | 4 ± 4 |
| Lys | 18 ± 2 |
| Arg | 12 ± 2 |
| Cys | 10 ± 2 |
| Pro | 29 ± 4 |

A portion of the fraction from Step 9 (1 μg) showing highest peak was exposed to 2% sodium dodecyl sulfate (SDS) with and without 5% β-mercaptoethanol at neutral pH in a boiling water bath for 2-3 minutes; both aliquots were subsequently applied to a slab gel and subjected to SDS polyacrylamide gel electrophoresis (PAGE) as described by Laemmli, U.K., Nature, 227, 680-685 (1970). Protein bands were discovered by silver staining.

On SDS-PAGE under non-reducing condition, the inhibin protein showed a single band migrating at 32kD. Under reducing condition, the inhibin protein separated into two bands, one migrating at 18kD and the other at 14 kD. Electrophoresis showed the protein was more than 90% pure.

$NH_2$-terminal sequence analyses of the 18 kD and 14 kD chains of the 32 kD inhibin protein were accomplished by first separating the two chains by SDS-PAGE under reducing conditions. Microsequencing, as described in Spiess, J. et al. Biochemistry, 20, 1982-1988 (1981), of the intact inhibin protein beginning at the $NH_2$-terminus consistently revealed two residues of approximately equal concentration at every cycle, indicating that the protein is composed of two chains. Based upon the results from multiple sequencing analyses of both the intact and reduced inhibin protein, the sequence of the $NH_2$-terminal residues of the 18 kD chain of the inhibin protein is Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val. The first four $NH_2$-terminal residues of the 14 kD chain of the inhibin protein are Gly-Leu-Glu-Cys, and it is believed that the next twenty-one residues are Asp-Gly-Ser-His-Asn-Leu-Asp-Ser-Arg-Gln-Gln-Phe-Phe-Ile-Asp-Phe-Arg-Leu-Ile-Gly-Trp.

Because a substantial portion of the sequence of both chains of an inhibin protein is known, the mRNA encoding the chains can be isolated, and the cDNA's can be synthesized by recombinant DNA techniques. Messenger RNA (mRNA) is obtained from ovarian follicules which produce inhibin, and then cDNA is synthesized from the mRNA by reverse transcription. The cDNA is inserted into a cloning vector which is used to transform a suitable host to create a cDNA library.

Based upon the known partial amino acid residue sequence of the inhibin chains, labelled oligonucleotides are synthesized for detecting cDNA corresponding to each chain. Because of the degeneracy of the genetic code, mixed hybridization probes are prepared and used as probes. These probes are then used to select, from the library, cDNA clones that contain gene sequences encoding the chains. cDNA libraries may also be screened by immunological expression assay with an antibody raised against inhibin or one of the two inhibin chains. Immunological expression assay may also be used to confirm screening with hybridization probes.

From selected clones, cDNA is excised and inserted into appropriate vectors under the control of suitable promotor sequences, and the vectors are transformed into cell lines for expression of the recombinent inhibin chains. Although vectors containing the genes for both chains could conceivably be transformed into the same cell line, for simplicity, vectors for expression of each chain are preferably transformed separately into cell lines. The two inhibin chains can then be isolated from the cellular material and/or the cell culture medium. The two chains are then subjected to oxidizing conditions which promote disulfide bonding between the chains.

The foregoing molecular biology techniques may also be used to read the gene sequences encoding the separate inhibin chains, and thereby completely characterize the protein chains. By reading such a partial gene sequence, it has been determined that one larger form of inhibin protein contains a precursor of the 18 kD chain, having a molecular weight of about 55,000 Daltons, linked to the 14 kD chain. The precursor chain is estimated to contain between about 305 to about 350 residues and to include the sequence: Ala-Arg-Pro-Pro-Ser-Gly-Gly-Glu-Arg-Ala-Arg-Arg-Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val.

Substantially pure 32 kD inhibin or the nontoxic salts thereof, combined with a pharmaceutically acceptable carrier to form a pharmaceutical composition, may be administered to mammals, including humans, either intravenously, subcutaneously, percutaneously, intramuscularly or orally for control of fertility, gonadotropin secretion or sex hormone production.

Furthermore antibodies raised against synthetic fragments of inhibin have been shown to neutralize the activity of purified inhibin. Thus passive (administration of antibodies) or active (administration of immunogenic inhibin as antigen) immunization methods could be employed to block endogenous inhibin and thereby elevate endogenous gonadotropin secretion and evert a profertility effect in human beings and other vertebrate animal species having inhibin of a similar polypeptide structure. Administration of inhibin induces decreased fertility in female mammals and decreases spermatogenesis in male mammals. Administration of a sufficient amount of inhibin induces infertility in mammals. Inhibin is also useful for tests to diagnose infertility.

In order to generate an antibody titer that is reactive with the inhibin protein so as to block its subsequent activity, synthetic conjugate molecules are produced which mimic the antigenic activity of inhibin, and the conjugate is exposed to a mammalian immune system, e.g., by inoculation into mammalian animals, for example rabbits, for the purpose of inducing the generation of antibodies reactive with the conjugate and also with the mimicked inhibin. The immune-response-inducing portion of the antigenic conjugate can be a synthetic peptide chain that is or contains a segment which is identical to or closely homologous to a segment of an inhibin protein chain. The portion of the inhibin chain to which the synthetic peptide segment is homologous should either be the active site of the inhibin protein chain or a site sufficiently close to the active site so that a bound antibody molecule inhibits hormonal activity of the inhibin protein, e.g., sterically. It has been surprisingly found that the six N-terminal residues of the 18 kD chain will create antibodies that are effective to inhibit the hormonal action of inhibin. The antigenic conjugate also includes a larger carrier moiety to which the synthetic peptide is linked, whereby the antigenic conjugate is sufficiently large to be recognized by the immune system of the inoculated animal, inducing its immune system to generate antibodies reactive with the conjugate.

Although inhibin itself is useful as an inoculum to induce the production of inhibin-reactive antibodies in a host animal, a synthetic antigenic conjugate which induces the production of antibodies that are also reactive with the endogenous inhibin molecule are preferred as inoculum. One major advantage of the use of a synthetic antigenic conjugate is the site-specificity which is achieved; whereas a synthetic inhibin antigen will only induce the production of antibodies reactive with the synthetic peptide chain and the mimicked portion of the inhibin molecule, the inhibin molecule induces the generation of antibodies reactive with a variety of antigenic determinants on the molecule. Accordingly, all inhibin-reactive antibodies that are induced by a conjugate containing a synthetic peptide and an appropriately selected mimicking peptide segment will neutralize inhibin, whereas some of the antibodies induced by natural inhibin protein may react with inhibin without neutralizing its hormonal activity. Because antibodies induced by an appropriate synthetic inhibin antigenic conjugate are all inhibin-deactivating, a lower titer may be administered to deactivate endogenous inhibin than a titer of antibodies that include antibody molecules which react with but do not inactivate or suppress hormonal activity. Minimizing the titer of inhibin-reactive antibody that is administered reduces the likelihood of inducing a significant immune response in the animal that is being treated.

Another important reason for avoiding the use of inhibin as inoculum for inducing the production of inhibin-reactive antibodies is that inhibin which is sufficiently pure to be used as inoculum is at this time very expensive. Because inhibin in itself is therapeutically useful, expenditure of this valuable material is desirably avoided.

It is well known to raise antibodies reactive with a proteinaceous material by synthesizing a short chain peptide corresponding to a portion of a protein chain of the material and linking the short chain synthetic peptide to a large carrier molecule so that the resulting peptide-carrier conjugate may be used as an antibody-inducing inoculum. Predictions have also been made as to which portions of a peptide chain would be expected to be immunogenically active; for example, it has often been suggested that peptide segments having a high proportion of hydrophillic amino acid residues can be expected to have a reasonable probability of being immunogenically active because such segments tend to align on the outside of the folded protein configuration in aqueous medium.

In practice, peptide-carrier conjugates have often proven to be much less suitable than desired for the purpose of inducing antibodies reactive with the endogenous protein. Reasons why such conjugates are often less than effective stimuli for generating antibodies to the endogenous protein are discussed at length by Jay A. Berzofsky, "Intrinsic and Extrinsic Factors in Protein Antigenic Structure", Science 229, 932–940 (1985). As discussed on page 936 of this article, antibodies induced by synthetic peptide conjugates may have two to three orders of magnitude lower affinity for the endogenous proteins than antibodies induced by the endogenous proteins.

It is therefore surprising that antibodies induced by synthetic antigenic conjugates in accordance with the present invention not only react with the endogenous inhibins but fully inactivate the hormonal activities of the inhibins. The strong inactivating effect of the conjugate-induced antibodies on endogenous inhibins gives them sufficient potency to be administered to mammalian animals for the purpose of significantly depleting the availability of endogenous inhibin protein and thereby enabling increased amounts of FSH to be secreted by the pituitary.

More specifically, it was surprising that a short peptide chain which contains the six residue N-terminal segment of the polypeptide 18 kD chain of a natural mammalian inhibin, when conjugated to a large carrier molecule, induces the production of antibodies that are not only reactive with the mammalian inhibin but fully inactivate the mammalian inhibin which the synthetic peptide chain segment mimics. Thus, in assays using pituitary cell cultures in which inhibin protein is shown to inhibit secretion of FSH by the cells, the presence of (1) antibodies raised against the peptide-carrier conjugate plus (2) the inhibin results in supression of inhibin activity and restores the level of secretion of FSH from the pituitary cell culture.

To antigenically activate and induce the production of antibodies having specific reactivity with inhibin, the synthetic peptide should have at least about six amino acid residues identical to the amino acid residue sequence of the N-terminus. The synthetic peptide is attached at its C-terminus, or at least downstream from the N-terminal residue, to the carrier molecule in order that the N-terminus of the synthetic peptide is outwardly exposed in the fashion of the N-terminus of the polypeptide chain of the natural inhibin molecule. To facilitate linking of the synthetic peptide to the carrier, the peptide may contain an amino acid residue at or closely adjacent to its C-terminus that can be linked by known linking chemicals to the carrier molecule, a C-terminal tyrosine (Tyr) being frequently used for this purpose. One or more additional amino acid residues may be included intermediate within the synthetic peptide sequence to space the N-terminal mimicking sequence from the C-terminal peptide by which the peptide is linked to a carrier. The amino acid residue by which the peptide is linked to the carrier need not be the amino acid at the C-terminus of the synthetic peptide, but for purposes of the present invention, adding additional amino acid residues at the C-terminus beyond the linking residue is considered generally extraneous.

The carrier molecule functions to provide the conjugate with sufficient size so that the conjugate is recognized by the immune system of the animal into which the conjugate is inoculated. Generally, to be recognized, the carrier should have a molecular weight of at least about 10,000 Daltons and preferably at least about 60,000 Daltons. An important attribute of a carrier molecule is that it is itself not strongly inducing of immune responses in the animal that is inoculated for antibody-generating purposes, whereby the primary immune response induced by the conjugate is to generate antibodies reactive with the synthetic peptide. A suitable carrier molecule is alpha-immunoglobulin obtained from a mammalian species. Other suitable carrier molecules include, but are not limited to, keyhole limpet hemocyanin, mammalian serum albumin, e.g., bovine serum albumin, amino acid polymers, e.g., polylysine, polyarginine and amino acid copolymers, e.g., glutamic acid-lysine copolymer.

Unless the C-terminus of the synthetic peptide is chemically reactive directly with a functional group on the carrier molecule, a linking molecule (or molecules) is used to link the C-terminus of the synthetic peptide to the carrier molecule. Bisdiazotized benzidine (BDB) is used to link C-terminal tyrosines of synthetic peptides to alpha immunoglobulin. BDB binds the tyrosine residue to tyrosine sidechains on the carrier protein molecule. Other linking chemical agents which may be used include glutaraldehyde for amino-to amino coupling, water-soluble carbodiimides for carboxyl-to-amino coupling and maleimidobenzoyl-N-hydrosuccinimide ester for coupling cysteine sulfhydryls to amino groups. The choice of linking groups depends upon available side chains and are also selected so as not to alter the mimicking protein segment against which antibodies are raised. For example if the mimicking segment contains a tyrosine, a linking agent other than BDB is preferably selected.

The presence of tyrosine in the synthetic peptide also permits labeling of the completed peptide with radioactive iodine, e.g., $^{125}I$, by iodination of the tyrosine residue.

Synthesis of short peptide chains useful for producing synthetic inhibin antigen are known in the art and will not be described in detail herein, reference being made to known protocols, such as W. Marki et al., J. Am. Chem. Soc. 103, 3178–2185 (1981). Peptides suitable for making synthetic inhibin antigenic conjugates according to the present invention may be less than ten amino acid residues long; however, peptides of about 25 residues may also be used. The art of making synthetic peptides is sufficiently advanced that these amino acids can be custom-ordered from certain biological supply houses, such as Bachem, Torrance, Calif. and Penninsula Laboratories, Belmont, Calif.

Inhibin-reactive antibodies and inhibin-mimicking antigenic substances are useful in immunoassay procedures for determining the level of endogenous inhibin in a mammalian fluid specimen. An initial use of inhibin-reactive antibodies and inhibin-mimicking substances is to determine the levels of endogenous inhibin in mammalian serum, abnormal inhibin levels being indicative of a hormonal cause of fertility problems. In determining the level of inhibin in mammalian fluid specimens, inhibin-mimicking substances compete with endogenous inhibin for binding sites of inhibin-reactive antibodies. Either the synthetic peptides alone or the conjugates are useful in such competitive immunoassays; however, in immunoassays, non-conjugated synthetic peptides are the preferred inhibin-mimicking substance.

Immunoassays include solution-phase and solid-phase, and competitive and non-competitive immunoassays. They include enzyme-linked immunosorbant assays and radioimmunoassays. The immunoassays are carried out by methods known in the immunoassay art for determining the concentration of a particular antigen (i.e., inhibin) in a specimen.

One particular type of inhibin immunoassay according to the invention is a competitive solid-phase assay wherein a quantity of inhibin-mimicking synthetic peptide and an unknown quantity of inhibin in a fluid specimen compete for binding by an inhibin-specific antibody. As a means of distinguishing and separating the known synthetic peptide and unknown inhibin quantities, one of the peptide and the inhibin in the specimen is bound to a solid support (e.g., the inside wall of a microtiter plate well) while the other is maintained in solution. In the assay, an excess of the antibody is first incubated with and complexed with the entire amount of the support-bound substance, synthetic peptide or inhibin, and the substance in solution and, in a second step, the antibody remaining unbound is reacted with the other of the substances. In the first step, the complexing of antibody with one of the substances results in "inhibiting" antibody binding with the other substance in the second step.

The preferred of these competitive solid-phase immunoassays are ELISA's, such as that described by E. Engvall, et al., Method Enzymol., 70: 419-439 (1980). Thus, the amount of antibody not complexed in the first step, but complexed in the second, whether the amount is support-bound or in solution, is measured by (1) reacting it with an antibody, preferably a polyclonal, subclass non-specific antibody, that reacts with immunoglobulin of the same class (e.g., $I_gG$) and from the same species (e.g., mouse) as the inhibin-reactive antibody and that has been previously linked to or complexed with an enzyme, (2) separating the portion of immunoglobulin-enzyme complex that binds to the complex of antibody bound to inhibin or synthetic peptide from that portion which does not bind to the complex of antibody bound to inhibin or peptide, and (3) determining the amount of enzyme in either portion by exposing the same to a reagent or reagents which undergo a chromogenic reaction in the presence of the enzyme. The relative amounts of antibody binding to the known synthetic peptide and unknown inhibin quantities is a function of the unknown quantity of endogenous inhibin in the fluid specimen, and this quantity is determinable by comparison with a standard curve that is derived by assaying serial dilutions of known synthetic peptide or inhibin concentrations by the same procedure.

Radioimmunoassays represent another suitable technique whereby inhibin in an unknown specimen may be quantitated. For example, the labeling of the synthetic peptide might be with a radioisotope, such as $^{125}I$, e g., through a tyrosine residue, rather than an enzyme, and the amount of labeled peptide measured (via radioactive emission). Iodination of a tyrosine residue of a synthetic peptide by the chloramine T method, purification of the iodinated synthetic peptide by cartridge extraction and HPLC, and use of the labeled synthetic peptide as a tracer in radioimmunoassay is described in Vale et al., "Neuroendocrine Peptides" Methods in Enzymology, Academic Press, N.Y. (1983).

The invention will now be described in greater detail by way of specific example.

EXAMPLE 1

The octapeptide H-Ser-Thr-Ala-Pro-Leu-Pro-Gly-Tyr-OH [pIN(alpha)(1–6)-Gly-Tyr] is synthesized by the protocol described in W. Marki et al. (1981) supra. The first six amino acid residues correspond directly to the first six amino acid residues of the N-terminus of the alpha chain of 32 kD porcine inhibin. Tyrosine in the eighth position serves as the means by which the peptide is conjugated to immunoglobulin, and glycine at the seventh position spaces the six-residue mimicking sequence from the tyrosine residue. The synthetic peptide was made using the Merrifield synthesis and purified on (HPLC) according to the method of J. Rivier et al., J. Chrom. 288, 303–328 (1984). Amino acid composition gave the expected ratio. Measurement of optical rotation gave $[a]_D = -118.5°$ (c=1, 1% AcOH). The purity of the peptide pIN(alpha)(1–6)-Gly-Tyr was greater than 98% as determined by analytical HPLC.

The synthetic peptide was coupled to human alpha-immunoglobulin through BDB, generally as described previously by W. Vale et al., Methods in Enzymology "Neuroendocrine Peptides", pp 565-577 Academic Press, N.Y. (1983). Through this process approximately 50 of the synthetic peptide moieties are bound to each immunoglobulin moiety.

To raise antibodies, rabbits were inoculated every two weeks with intravenous injections of 250 $\mu$g of conjugate in 1 ml. of equal volumes of saline and Freund's complete adjuvent. One week following the third inoculation, bleedings were made and the serum saved. Antiserum from each rabbit was characterized with respect to titer and affinity for H-Ser-Thr-Ala-Pro-Leu-Pro-Gly-$^{125}$I-Tyr-OH. The antibody titer ($Ab_1$) used for immunoneutralization bound 21% of the labeled peptide at 1:3000 final dilution.

The neutralizing effect on inhibin of porcine inhibin-reactive antiserum $Ab_1$ was measured by in vitro assay, which assay is based upon the level of secretion by cultured rat anterior pituitary cells as described in W. Vale et al., Endocrinology 91, 562–572 (1972) and G. F. Erickson, et al. Endocrinology 103, 1960–1963 (1978). Pituitary cells are enzymatically dispersed and plated into 24-well Linbro tissue culture plates supplied with Dulbecco's modified Eagles medium (DMEM) at $5\times10^5$ cells per well. After washing the cells three times, the cell cultures are incubated in 3 ml DMEM for 2½ hours at 37° C. with combinations of inhibin (IN) (0.55 ng), normal rabbit serum (NRS) (50 $\mu$l) and $Ab_1$ (50 $\mu$l), as set forth in Table 1 below. Table I shows the ng of FSH/ml±SEM (p less than 0.01) secreted per well based upon the average of three wells for each combination.

TABLE 1

Control: 63.4±3.0
NRS: 55.9±1.4
$Ab_1$: 65.5±1.4
IN: 23.4±1.4
IN+NRS: 23.1±1.0
IN+$Ab_1$: 43.7±1.3

These results show that, whereas inhibin depresses basal level secretions of FSH from pituitary cells, antiserum raised against the conjugate neutralizes the activity of inhibin. Neither NRS nor $Ab_1$ affects the basal level of FSH-secretion. NRS has no effect on the FSH-releasing inhibition action of inhibin. The suppression of inhibin activity by $Ab_1$, as evidenced by restoration of the amount of FSH released in the wells containing both IN and $Ab_1$ as compared to the wells containing only IN, shows that $Ab_1$ binds with and neutralizes porcine inhibin.

EXAMPLE 2

The peptide H-Gly-Leu-Glu-Cys-Asp-Gly-Arg-Tyr-OH [pIN(beta)(1-7)-Tyr] containing the first seven amino acid residues of the beta chain of 32 kD porcine inhibin plus tyrosine is synthesized and conjugated to human alpha-immunoglobulin as described in Example 1. The conjugate is used to raise antibodies in rabbits according to the procedure outlined in Example 1. Antisera raised against the conjugate neutralize the activity of porcine inhibin in the manner of $Ab_1$ in Example 1.

EXAMPLE 3

The peptide H-Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Gly-Tyr-OH [pIN(alpha)(1-25)-Gly-Tyr] is synthesized and conjugated to human alpha immunoglobulin as described in Example 1. The first 25 residues of the peptide correspond to the N-terminus of the alpha chain (18 kD chain) of porcine inhibin. The conjugate is used to raise antibodies in rabbits according to the procedure outlined in Example 1. Porcine inhibin supresses basal levels of FSH-secretion in rat anterior pituitary cultures, and antisera raised against this conjugate neutralize the activity of porcine inhibin.

EXAMPLE 4

The peptide H-Ser-Thr-Pro-Leu-Met-Ser-Gly-Tyr-OH [hIN(alpha)(1-6)-Gly-Tyr] is synthesized and conjugated to human alpha immunoglobulin as described in Example 1. The first six residues of the peptide correspond to the N-terminus of the alpha chain (18 kD chain) of 32 kD human inhibin. The conjugate is used to raise antibodies in rabbits according to the procedure outlined in Example 1. Human inhibin supresses basal levels of FSH-secretion in rat anterior pituitary culture. Antisera raised against the conjugate neutralize the activity of human inhibin.

EXAMPLE 5

Antibodies raised in Example 3 are used in vivo to see the neutralization effects upon endogenous inhibin levels by administration to adult female rats. The rabbit antiserum generated using the synthetic peptide described in Example 3 is administered, and the levels of FSH are monitored.

The antiserum obtained from the inoculated rabbit in Example 3 is diluted 1:1 in 0.05 M sodium carbonate-bicarbonate buffer, pH 9.6. The diluted antiserum is fed through indwelling venous catheters in the jugular and femoral vein at the rate of 0.2 ml per hour using a Harvard 2265 Multiple Syringe Pump. The infusion was carried out for 15 hours beginning at 12 noon on the day of proestrus. Blood samples were taken each hour and replaced with an equivalent volume of reconstituted red blood cells.

Monitoring was carried out for 24 hours until 2 noon of estrus, and these rats were compared with rats which received injections of normal rabbit serum. Whereas the NRS-injected rats showed two peaks of plasma FSH values at 4 to 5 PM and at 12 AM, the rats receiving the antibody showed a sustained increase in plasma FSH beginning 3 hours after the start of infusion and remained statistically different, i.e., higher, throughout the rest of the treatment. When the infusion stopped after 15 hours, the level of FSH began a linear decline but remained higher than those which received only NRS injections. Thus, the test showed that the antibodies are effective to neutralize the biological effect of inhibin.

EXAMPLE 6

Additional testing with the antibodies used in Example 5 was carried out using 20 and 30 day old rat pups, each of which was injected i.v. with either NRS or with the antibody serum. In the test, 0.4 ml was administered to the day-20 rats and 0.8 ml was administered to the day-30 rats. Both the day-20 and day-30 rats had significant amounts of endogenous inhibin being released. The antibody serum exhibited a significant effect, causing an elevation in FSH levels from about 8.3 ng/ml to about 14.4 ng/ml in the 20-day old rats and an elevation of from about 4.7 ng/ml to about 8.8 ng/ml in the 30-day old rats. Again the tests showed that the antibodies are effective in neutralizing the biological effect of inhibin.

Although the above Examples relate to conjugates in which the synthetic peptides mimic the N-termini of inhibin chains, conjugates having peptides which mimic other portions of inhibin chains may be used to induce antibodies which react with inhibin proteins, and the use of such other conjugates which induce the generation of inhibin-reactive and inhibin-inactivating antibodies are considered to be within the scope of the present invention.

Also considered to be within the scope of the invention is the use of monoclonal antibodies that react with inhibin and thereby suppress its FSH-release-inhibiting activity. Antisera induced in accordance with the present invention may be immortalized by conventional hybridoma-producing protocols. Because polyclonal antisera raised against conjugates are site-specific, i.e., react with those specific portions or sites of the endogenous polypeptide chains that are mimicked by the synthetic peptides, there may be no particular advantage to using monoclonals rather than polyclonals with respect to site-specificity. Nevertheless, monoclonal antibodies do provide a uniformity not provided by polyclonals, and monoclonal antibodies which do not induce undesirable immunological reactions in the species being treated may be preferred for in vivo administration. Furthermor, monoclonal antibody titers may contain less immunologically active extraneous material than antisera raised in inoculated animals.

It is desirable to purify antibody titers prior to administration to animals for control of fertility. The synthetic peptides which are used for forming the antigenic conjugates may also be used as a basis for antibody purification by affinity chromatography. The synthetic peptides are linked to conventional solid support material and the support material then packed as chromatography columns. Antisera is exposed to the column under conditions which allow antibody molecules to bind with the synthetic peptide moieties, and then the column is washed with solution that releases the antibodies from the column. Vice-versa, antibodies may be used to extract inhibin from impure bodily extracts using the protocols of immunoaffinity chromatography.

Although the generation of inhibin-reactive antisera described herein is a conventional animal-inoculation procedure, it is also considered to be within the scope of the present invention to induce the production of inhibin-reactive antibodies in vitro by cultured cells, such as by the protocol described by B. Boss, *Brain Research* 291, 193-196 (1984).

Antibodies reactive with inhibin are useful for administering to animals to neutralize the activity of endogenous inhibin and thereby elevate endogenous gonadotropin secretion and exert a profertility effect in human beings and other mammalian animal species having inhibin of a similar structure. Administration of titers of inhibin-reactive antibody increases fertility in female animals and increases spermatogenesis in male animals. To substantially affect secretion levels of gonadotropins in mammalian animals, sufficient antibody is administered daily to react with and neutralize between about 80 and about 130 nM of inhibin protein per kilogram of body weight. The actual titer of antibody administered depends on the affinity of the particular antibody for inhibin, and in general, between about 20 and about 200 nM of inhibin-reactive antibody is administered daily per kilogram of body weight of a treated animal.

Antibodies effective for the suppression of inhibin levels are generally administered intravenously, resulting in inhibin neutralization in the peripheral blood serum, whereupon the gonadally-secreted inhibin does not reach the pituitary in active form. Effective dosages of antibody neutralize up to about 90 percent of the endogenous inhibin found in the peripheral blood serum. Inhibin-reactive antisera may be administered as harvested, e.g., from an antibody or in the case of monoclonal antibodies from hybridoma supernatent, without dilution, but is typically administered along with a suitable diluent, such as isotonic saline, phosphate buffer solutions or other isotonic salt preparations.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

Various features of the invention are emphasized in the following claims.

What is claimed is:

1. Antibodies generated by a mammalian immune system in response to exposure to a synthetic peptide including the amino acid residue sequence of the six N-terminal residues of the alpha chain of a natural mammalian inhibin protein, which specifically bind to mammalian inhibin protein and block the hormonal activity of endogenous inhibin.

2. Antibodies according to claim 1 which are generated by exposure to a conjugate comprising said synthetic peptide and a carrier molecule to which said synthetic peptide is linked.

3. Antibodies according to claim 2 wherein said synthetic peptide is an octapeptide comprising the first six N-terminal residues of the alpha chain of a natural mammalian inhibin, a spacer amino acid in the 7-position, and a carboxyl terminus amino acid suitable for linking said synthetic peptide to said carrier molecule.

4. Antibodies according to claim 1 wherein said synthetic peptide includes the N-terminus of porcine inhibin alpha chain.

5. A method of treating a mammalian animal to control fertility comprising generating an antibody titer by generating an immune response using a synthetic peptide including the six N-terminal residues of a mammalian inhibin alpha chain, which antibody reacts with inhibin and thereby counteracts the gonadotropin-release-suppressing activity of inhibin, and administering said antibody titer to a mammalian animal at a dosage sufficient to neutralize a significant proportion of the inhibin level in the peripheral blood serum.

6. A method according to claim 4 wherein between about 20 nM and about 200 nM of inhibin-reactive antibody is administered per kilogram of body weight per day.

7. A method according to claim 4 wherein said antibodies are generated by linking said synthetic peptide to a carrier molecule to produce a conjugate of sufficient size to stimulate antibody-producing cells of a mammalian immune system, exposing said conjugate to the mammalian immune system and collecting antiserum generated by the immune system.

8. A method according to claim 6 wherein said synthetic peptide includes the sequence of the N-terminus of the alpha chain of porcine inhibin.

9. A method according to claim 7 wherein said carrier molecule is alpha immunoglobulin.

10. A conjugate for inducing the production of inhibin-reactive antibodies by a mammalian immune system comprising a synthetic peptide including a selected amino acid residue sequence of the alpha chain of a natural mammalian inhibin protein chain and a carrier molecule to which said synthetic peptide is linked, said carrier molecule having sufficient size so that said conjugate stimulates antibody-producing cells of a mammalian immune system to generate antibodies reactive with said mimicking sequence.

11. A conjugate according to claim 9 wherein said sequence includes the six N-terminal residues of porcine inhibin.

12. A conjugate according to claim 9 wherein said sequence is the N-terminus of human inhibin.

13. A conjugate according to claim 10 wherein said carrier molecule is a mammalian alpha immunoglobulin.

14. A conjugate according to claim 9 also including a moiety at one end of said sequence linking said peptide to said carrier molecule.

15. A conjugate according to claim 9 wherein said synthetic peptide includes a tyrosine residue and said peptide is linked to said carrier molecule through said tyrosine residue.

* * * * *

UNITED STATES PATENT AND TRADEMARK OFFICE
CERTIFICATE OF CORRECTION

PATENT NO.  : 4,864,019
DATED       : September 5, 1989
INVENTOR(S) : Vale et al.

It is certified that error appears in the above-identified patent and that said Letters Patent is hereby corrected as shown below:

<u>IN THE ABSTRACT:</u>
    Line 12, change "-G y" to -- -Gly- --.

<u>IN THE SPECIFICATION:</u>
    Column 1, line 61, Change "flui(pFF)" to --fluid (pFF)--.
    Column 2, line 11, Change "(1H)" to --(LH)--.
    Column 3, line 29, Change "1H" to --LH--.
    Column 6, line 3, Change "withninhydrin" to --with ninhydrin--.
    Column 6, lines 3-4, Change "derivation" to --derivatization--.
    Column 10, line 26, Change "amino-to amino" to --aminq-to-amino--.
    Column 14, line 47, Change "Furthermor" to --Furthermore--.

<u>IN THE CLAIMS:</u>
    Claim 11, Column 16, line 43, Change "9" to --10--.
    Claim 12, Column 16, line 46, Change "9" to --10--.
    Claim 13, Column 16, line 48, Change "10" to --11--.
    Claim 14, Column 16, line 50, Change "9" to --10--.
    Claim 15, Column 16, line 53, Change "9" to --10--.

Signed and Sealed this

Twenty-fifth Day of September, 1990

Attest:

HARRY F. MANBECK, JR.

*Attesting Officer*    *Commissioner of Patents and Trademarks*